United States Patent [19]

Thomas

[11] 4,265,805

[45] May 5, 1981

[54] POLYMERIC LIGHT STABILIZERS CONTAINING TETRALKYL PIPERIDINE MOIETIES

[75] Inventor: Richard W. Thomas, Piscataway, N.J.

[73] Assignee: American Cyanamid Company, Stamford, Conn.

[21] Appl. No.: 136,207

[22] Filed: Apr. 1, 1980

[51] Int. Cl.³ .................... C07D 401/14; C08G 18/38; C08K 5/34
[52] U.S. Cl. .............................. 260/45.8 N; 106/176; 525/184; 528/73; 528/327; 546/16; 546/188; 546/189
[58] Field of Search ................ 260/45.8 NP; 525/184; 528/73, 327; 546/16, 188, 189

[56] References Cited

U.S. PATENT DOCUMENTS

| | | | |
|---|---|---|---|
| 3,971,795 | 7/1976 | Cook ...................................... | 546/16 |
| 4,064,102 | 12/1977 | Hillard et al. ........................ | 546/188 |
| 4,091,000 | 5/1978 | Schmidt ................................ | 528/73 |
| 4,102,870 | 7/1978 | Hofmann et al. ..................... | 528/73 |
| 4,145,512 | 3/1979 | Uhrhan et al. ........................ | 528/73 |
| 4,153,596 | 5/1979 | Oertel et al. .......................... | 528/73 |

*Primary Examiner*—Hosea E. Taylor
*Assistant Examiner*—R. A. White
*Attorney, Agent, or Firm*—Bruce F. Jacobs

[57] ABSTRACT

Polymeric polyesters containing a 2,2,6,6-tetralkyl piperidine moiety in the repeating unit are disclosed as light stabilizers for polymers subject to degradation by ultra-violet light.

14 Claims, No Drawings

POLYMERIC LIGHT STABILIZERS CONTAINING TETRALKYL PIPERIDINE MOIETIES

This invention relates to novel polyester light stabilizers, polymer compositions stabilized by said polyesters, and a process for stabilizing polymers against degradation by light. More particularly, the invention pertains to novel polyesters represented by formula (I)

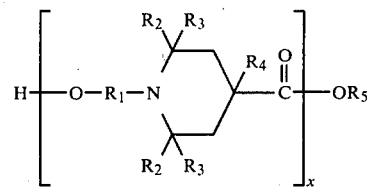

wherein $R_1$ is alkylene ($C_2$–$C_8$) or cycloalkylene ($C_5$–$C_6$); $R_2$ and $R_3$ are each alkyl ($C_1$–$C_8$) or together with the carbon to which they are attached form a cycloalkyl ring ($C_5$–$C_6$); $R_4$ is hydrogen, hydroxyl, alkoxy ($C_1$–$C_8$), or acyloxy ($C_1$–$C_8$); $R_5$ is alkyl ($C_1$–$C_8$) or cycloalkyl ($C_5$–$C_6$); and x is an integer from 4 to about 10.i Preferably, $R_1$ is alkylene ($C_2$–$C_4$), $R_2$ and $R_3$ are alkyl ($C_1$–$C_4$), $R_4$ is hydrogen, hydroxyl, or alkoxy ($C_1$–$C_4$), $R_5$ is alkyl ($C_1$–$C_3$), and x is an integer of about 6 to 8. Most preferably, $R_1$ is ethylene, $R_2$ and $R_3$ are methyl, $R_4$ is hydroxyl and $R_5$ is methyl.

The invention also relates to the use of these polyesters as stabilizers against photo- and thermal degradation, particularly against degradation induced by UV light, of synthetic polymers, especially polyolefins. The invention further relates to polymer compositions stabilized by the incorporation therein of said polyesters.

Esters containing the 2,2,6,6-tetralkyl piperidene moiety have been disclosed in the patent literature as stabilizers for polymers.

U.S. Pat. No. 4,064,102 (Hillard et al.) describes esters of the formula (II)

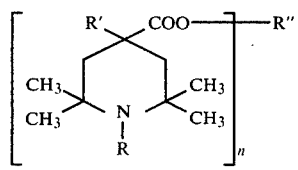

where R is H or alkyl ($C_1$–$C_8$); R' is hydrogen, hydroxyl, or alkoxy ($C_1$–$C_8$); R" is alkyl ($C_1$–$C_{20}$), alkylene ($C_2$–$C_{12}$), cycloalkyl, wherein the cycloaliphatic ring contains 5- or 6-carbon atoms, cycloalkylene, wherein the cycloaliphatic ring may contain lower alkyl substituents, arylene, aralkylene and alkenyl ($C_3$–$C_{20}$); and n is an integer from 1 to 4, which are useful for stabilizing polyolefins against photo and thermal degradation.

U.S. Pat. No. 3,640,928 (Murayama to Sankyo Company, Ltd.) discloses compounds represented by formula (III)

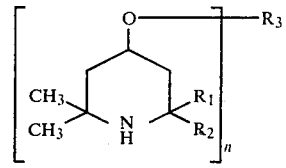

wherein $R_1$ and $R_2$ represent alkyl ($C_1$–$C_4$); $R_3$ is an acyl, diacyl, or triacyl group derived from aliphatic, alicyclic, or heterocyclic mono-, di-, or tricarboxylic acids; and, n is 1 to 3. However, the esters of formulas (II) and (III) have been found to bloom from polyolefin films containing the same during processing.

In has been now discovered that the polymeric esters of formula (I) provide satisfactory light stability while providing superior processing stability, by virtue of resistance to blooming and thermal decomposition, in synthetic polymers, particularly polyethylene and polypropylene, as compared to the prior esters of formulas (II) and (III).

The polymeric esters of formula (I) also have superior resistance to extraction, by water and organic solvents, from the synthetic polymer.

The polymers of formula (I) may be prepared by the condensation polymerization of an ester of formula (IV),

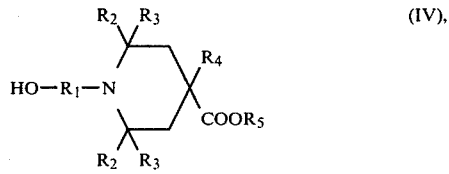

wherein $R_1$, $R_2$, $R_3$, $R_4$, and $R_5$ are as previously defined, at an elevated temperature in the presence of a conventional polymerization catalyst. Generally the temperature is about 130° to 200° C., most preferably about 140° to 150° C. Suitable polymerization catalysts include oxides of Group IV metals, alkali metal alkoxytitanates, tetraalkyltitanate esters, tetraalkyl-tin compounds and alkaline earth salts of weak acids such as:
  titanium (IV) isopropoxide,
  titanium (IV) butoxide,
  titanium (IV) 2-ethylhexyloxide,
  tetrabutyltin,
  tetramethyltin,
  antinomy trioxide, and
  manganese acetate.
Preferably the catalyst is titanium (IV) isopropoxide.

The intermediate esters of Formula (IV) can be prepared by reacting a compound of formula (V)

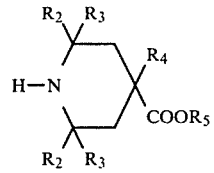

with an appropriate hydroxy-substituted alkyl halide, or alkylene oxide, under conditions well-known in the art.

The reaction with an alkylene oxide is carried out by heating the compound of formula (V) with the alkylene oxide in an alcohol of the formula R₅OH in the presence of a catalytic amount of hydrochloric acid in a pressure essel, stripping off the excess alcohol, and recovering ⌊.e compound of formula (IV).

Illustrative examples of the compounds of formula (IV) include the following:
(1) 4-carbomethoxy-1-(2-hydroxyethyl)-2,2,6,6-tetramethylpiperidine,
(2) 4-carbobutoxy-1-(2-hydroxyethyl)-2,2,6,6-tetraethylpiperidine,
(3) 4-carbooctyloxy-1-(2-hydroxyethyl)-2,2-dimethyl-6,6-diethylpiperidine,
(4) 4-carbethoxy-1-(2-hydroxypropyl)-2,6-dimethyl-2,6-diethylpiperidine,
(5) 4-carbomethoxy-1-(2-hydroxybutyl)-2,2,6-trimethyl-6-isohexylpiperidine,
(6) 4-carbomethoxy-1-(4-hydroxycyclohexyl)-2,2,6,6-tetrabutylpiperdine,
(7) 4-carbomethoxy-1-(2-hydroxyethyl)-2,2-dimethyl-1-azaspiro[5.5]undecane,
(8) 4-carbomethoxy-1-(2-hydroxyethyl)-2,2-dimethyl-1-azaspiro[5.5]decane,
(9) 4-carbomethoxy-4-hydroxy-1-(2-hydroxyethyl)-2,2,6,6-tetramethylpiperidine,
(10) 4-carbohexyloxy-4-hydroxy-1-(3-hydroxypropyl)-2,2,6-trimethyl-6-octylpiperidine,
(11) 4-carbomethoxy-4-hydroxy-1-(2-hydroxyhexyl)-2,2,6,6-tetramethylpiperidine,
(12) 4-carbomethoxy-4-hydroxy-1-(2-hydroxyoctyl)-2,2,6,6-tetramethylpiperidine,
(13) 4-carbomethoxy-4-hydroxy-1-(2-hydroxyethyl)-2,2-dimethyl-1-azaspiro[5.5]undecane,
(14) 4-carbomethoxy-4-methoxy-1-(2-hydroxyethyl)-2,2,6,6-tetramethylpiperidine,
(15) 4-carbomethoxy-4-butoxy-1-(2-hydroxypropyl)-2,2,6,6-tetramethylpiperidine,
(16) 4-carbomethoxy-4-octyloxy-1-(2-hydroxyhexyl)-2,2,6,6-tetramethylpiperidine,
(17) 4-carbomethoxy-4-methoxy-1-(2-hydroxyhexyl)-2,2-dimethyl-1-azaspiro[5.5]undecane,
(18) 4-acetyloxy-4-carbomethoxy-1-(2-hydroxyethyl)-2,2,6,6-tetramethylpiperidine,
(19) butyryloxy-4-carbethoxy-1-(2-hydroxybutyl)-2,2-dimethyl-6,6-diethylpiperidine,
(20) 4-carbomethoxyl-4-octanoyloxy-1-(2-hydroxyethyl)2,2,6,6-tetramethylpiperidine,
(21) 4-acetyloxy-4-carbomethoxy-1-(2-hydroxyethyl)-2,2-dimethyl-1-azaspiro[5.5]undecane,
(22) 15-carbethoxy-15-hydroxy-7-(2-hydroxyethyl)-7-azadispiro[5.1.5.3]hexadecane,
(23) 15-carbomethoxy-15-methoxy-7-(2-hydroxyethyl)-7-azadispiro[5.1.5.3]hexadecane, and
(24) 15-carbomethoxy-7-(2-hydroxypropyl)-7-azadispiro[5.1.5.3]hexadecane, and the like.

Illustrative of polymers which may be used as the polymeric substrate in the subject invention are such as the following: polypropylene, polyethylene, ethylene-propylene copolymers, ethylene-butylene copolymers, polybutylene, poly(vinyl chloride), poly(methyl methacrylate), aromatic polyurethanes, polystyrene, high impact poly(styrene), polycarbonate, poly(caprolactam), poly(hexamethylene adipamide), poly(hexamethyleneterephthalamide), poly(methyl acrylate), poly(ethylene terephthalate), cellulose acetate, poly(vinylidene chloride), butadiene-styrene copolymers, acrylonitrilestyrene copolymers, butadiene-acrylontrile-styrene copolymers and the like, and blends thereof.

The preferred materials are polypropylene and polyethylene.

The amount of the stabilizer of formula (I) needed to be an effective amount for stabilizing the polymer against degradation will depend on the nature of the polymer and the amount of exposure to ultraviolet radiation to which the article will be subjected. For most purposes, it is sufficient to use an amount of the stabilizer of formula (I) within the range of about 0.01 to about 5 percent by weight, preferably 0.1 to 2 percent by weight, based on the weight of untreated polymer.

The stabilizer may be incorporated in or on such polymer materials by any of the various procedures known in the art for such purpose, such as by dry blending the additive with the polymer in powder or granular form followed by milling, Banbury mixing, molding, casting, extruding, swelling, and the like; by immersing the polymer as film, sheet, fibers, etc. in a solution of the additive in an appropriate solvent (as in a dyeing process), etc.

The stabilizer of formula (I) may be used in the polymers alone or in combination with other conventional additives, such as fillers, antioxidants, flame retardants, heat stabilizers, antislipping and antistatic agents, supplemental light stabilizers, pigments, dyes, etc.

As with the stabilizer of formula (I), any further additive is advantageously employed in a proportion within the range standard in the art of from about 0.01 to about 5 percent by weight, preferably 0.1 percent to 2 percent by weight, based on the weight of untreated polymer.

Illustrative of suitable antioxidants useful with the present stabilizers are those of the hindered-phenol type, such as 2,6-di-t-butyl-p-cresol; 4,4'-bis(2,6-di-t-butylphenol); 4,4'-bis(2,6-di-iso-propylphenol); 2,4,6-tri-t-butylphenol; 2,2'-thiobis(4-methyl-6-t-butylphenol); octadecyl 2(3',5'-di-t-butyl-4'hydroxyphenyl)propionate; etc.; esters of thiopropionic acid, such as dilauryl thiodipropionate and distearyl thiodipropionate, etc.; hydrocarbyl phosphites, such as triphenyl phosphite, trinonyl phosphite, diphenyldecyl phosphite, etc.; and combinations thereof.

Illustrative examples of supplemental light stabilizers are those of the benzotriazole class, such as 2-(2'-hydroxy-5'-methylphenyl)benzotriazole; 2-(2'-hydroxy-3',5'-di-t-butylphenyl)-5-chlorobenzotriazole; those of the hydroxybenzophenone type, such as 2-hydroxy-4-methoxybenzophenone; 2-hydroxy-4-octyloxybenzophenone; 2,2'-dihydroxy-4,4'-dimethoxybenzophenone; hindered phenol esters, such as 2',4'-di-t-butylphenyl 3,5-di-t-butyl-4-hydroxybenzoate; metal complexes, such as nickel complexes of 2,2'-thiobis(4-t-octylphenol); nickel butylamine complex of 2,2'-thiobis(4-t-octylphenol); nickel complexes of bis(4-t-octylphenyl)sulfone; nickel dibutyl dithiocarbamate; nickel salts of 4-hydroxy-3,5-di-t-butyl-benzyl phosphonic acid monoalkyl esters where alkyl is methyl, ethyl, propyl, butyl, etc.; nickel complex of 2-hydroxy-4-methylphenyl-undecyl ketone oxime; etc. Further illustrative examples of suitable antioxidants and of suitable supplemental light stabilizers can be found in columns 3 and 4 of U.S. Pat. Nos. 3,488,290 and 3,496,134 and the other patents mentioned therein, all incorporated herein by reference.

The following examples are presented to further illustrate the present invention. All parts and percents are by weight unless otherwise specified.

EXAMPLE 1

Polymerization of 4-Carbethoxy-1-(2-hydroxyethyl)-2,2,6,6-tetramethylpiperidine 4-Carbethoxy-1-(2-hydroxyethyl)-2,2,6,6-tetramethylpiperidine (12.1 grams; 0.047 mole) and titanium (IV) isopropoxide (0.2 ml) are stirred and heated at 170° C. under a blanket of nitrogen for 3 hours. Vacuum is then applied to the reaction vessel and the temperature is raised to 200° C. After heating under vacuum at 200° C. for 2 hours, the reaction product is cooled to room temperature, pulverized, washed with ethanol 3-A and air dried. The product (8.8 grams; 89% of theoretical) has a nuclear magnetic resonance spectrum consistent with a condensation polymer of the starting material. The polymer has a molecular weight of about 1000-2000, i.e. x is about 5-10.

Polymers are also obtained in a similar manner by substituting the compounds of formula (IV) numbered (4), and (7), respectively, for the 4-carbethoxy-1-(2-hydroxyethyl)-2,2,6,6-tetramethylpiperidine.

EXAMPLE 2

Polymerization of 4-Carbomethoxy-4-hydroxy-1-(2-hydroxy-ethyl)-2,2,6,6-tetramethylpiperidine 4-Carbomethoxy-4-hydroxy-1-(2-hydroxyethyl)-2,2,6,6-tetramethylpiperidine (9.4 grams; 0.036 mole) is heated to 140° C. and titanium (IV) isopropoxide (0.2 ml) is added thereto. The mixture is heated at 140° C. for one hour and vacuum is then applied to the system. After heating the reaction mixture for 3 hours under vacuum, the temperature is raised to 200° C. and heating is continued for an additional 3 hours. The reaction product is then cooled to room temperature, triturated with hot water, and dried to obtain 3.7 grams of product. The degree of polymerization x is about 5-10.

Polymers are also obtained in a similar manner by substituting the compounds of formula (IV) numbered (11), (12), (14), (16), and (20), respectively, for the 4-carbomethoxy-4-hydroxy-1-(2-hydroxyethyl)-2,2,6,6-tetramethylpiperidine.

EXAMPLES 3-5

The additives (0.25 gram), as prepared in Examples 1 and 2, were each dry blended on a two-roll mill with unstabilized polypropylene (100.0 grams of Pro-fax 6401; Hercules Inc., Wilmington, Del.) along with 2,4,6-tri-t-butylphenol (0.10 gram), a processing antioxidant. The dry blend was milled at 350°-375° F. for 4 minutes and the milled sample was compression molded at 400° F. into films about 4-5 mils thick.

The films were exposed to a carbon arc in a Color Fade-Ometer and a Xenon Arc Weather-Ometer (Atlas Electric Devices Company, Chicago, Ill.) until and each film showed an increase in carbonyl content of 0.1% by weight, as determined by infrared spectrophotometry. This level of carbonyl content coincides with the point of embrittlement of the film. The following results were obtained:

| Example | Additive | Hours to Increase Carbonyl Content 0.1% | |
|---|---|---|---|
| | | Fade-Ometer | Weather-Ometer |
| 3 | Product of Example 1 | 700 | 1200 |
| 4 | Product of Example 2 | 900 | 1200 |
| 5 | None | 400 | 500 |

No blooming was observed with these films.

In the manner described above, substitution of 0.25 gram of the polymers obtained by polymerization of compounds (4), (7), (11), (12), (14), (16), (18), and (20), respectively, as the additive gives similar results.

EXAMPLE 6

The procedure of Examples 3-5 was repeated to demonstrate that the prior art compounds do indeed bloom in polypropylene.

The following compounds of U.S. Pat. No. 4,064,102 were tested at a concentration of 0.25% by weight:
- stearyl 2,2,6,6-tetramethylpiperidine-4-carboxylate
- 1,4-butylene 2,2,6,6-tetramethylpiperidine-4-carboxylate
- 1,3-propylene 2,2,6,6-tetramethylpiperidine-4-carboxylate All of these compounds bloomed.

The following compounds of U.S. Pat. No. 3,640,928 were tested at a concentration of 0.5% by weight:
- 4-stearyloxy-2,2,6,6-tetramethylpiperidine
- 4-dodecanoyloxy-2,2,6,6-tetramethylpiperidine
- 4octanoyloxy-2.2.6.6-tetramethylpiperidine
- 4-benzoyloxy-2,2,6,6-tetramethylpiperidine
- bis(2,2,6,6-tetramethyl-4-piperidyl)adipate All of these compounds bloomed. In addition the adipate was tested at a concentration of 0.1% and it still bloomed.

What is claimed is:

1. A polymer of the formula

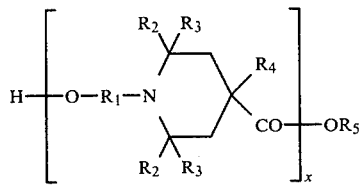

wherein $R_1$ is alkylene ($C_2$-$C_8$) or cycloalkylene ($C_5$-$C_6$); $R_2$ and $R_3$ are each alkyl ($C_1$-$C_8$) or together with the carbon to which they are attached form a cycloalkyl ring having 5 or 6 carbon atoms; $R_4$ is hydrogen, hydroxyl, alkoxy ($C_1$-$C_8$), or acyloxy ($C_1$-$C_8$); $R_5$ is alkyl ($C_1$-$C_8$) or cycloalkyl ($C_5$-$C_6$); and, x is an integer from 4 to about 10.

2. The polymer of claim 1 wherein $R_1$ is alkylene ($C_2$-$C_4$), $R_2$ and $R_3$ are each alkyl ($C_1$-$C_4$), $R_4$ is hydrogen hydroxyl or alkoxy ($C_1$-$C_4$), $R_5$ is alkyl ($C_1$-$C_3$), and x is about 6-8.

3. The polymer of claim 1 wherein $R_2$ and $R_3$ are each methyl.

4. The polymer of claim 3 wherein $R_4$ is hydroxyl.

5. The polymer of claim 1 wherein $R_1$ is ethylene, $R_2$ and $R_3$ are methyl, $R_4$ is hydroxyl, and $R_5$ is methyl.

6. A composition comprising a polymer normally subject to degradation by ultraviolet light and an ultraviolet stabilizingly effective amount of a polymer of claim 1.

7. The composition of claim 6 wherein $R_1$ is alkylene ($C_2$–$C_4$), $R_2$ and $R_3$ are each alkyl ($C_1$–$C_4$), $R_4$ is hydrogen or hydroxyl, $R_5$ is alkyl ($C_1$–$C_3$) and x is about 10.

8. The composition of claim 7 wherein $R_2$ and $R_3$ are each methyl.

9. The composition of claim 8 wherein $R_4$ is hydroxyl.

10. The composition of claim 6 wherein $R_1$ is ethylene, $R_2$ and $R_3$ are methyl, $R_4$ is hydroxyl and $R_5$ is methyl.

11. The composition of claim 6 wherein said effective amount is about 0.01% to about 5% by weight of said stabilizer based on the weight of said polymer.

12. The composition of claim 6 wherein said polymer is a polyolefin.

13. The composition of claim 12 wherein said polyolefin is polypropylene.

14. The composition of claim 6, wherein said polymer is selected from the group consisting of polyethylene, a copolymer of ethylene and propylene, and an aromatic polyurethane.

* * * * *